US00PP23633P2

(12) United States Plant Patent
Tobutt

(10) Patent No.: US PP23,633 P2
(45) Date of Patent: May 28, 2013

(54) ***SAMBUCUS* PLANT NAMED 'EIFFEL 1'**

(50) Latin Name: *Sambucus nigra*
Varietal Denomination: Eiffel 1

(76) Inventor: Kenneth Richard Tobutt, Gravesend (GB)

( * ) Notice: Subject to any disclaimer, the term of this patent is extended or adjusted under 35 U.S.C. 154(b) by 243 days.

(21) Appl. No.: 13/068,783

(22) Filed: May 20, 2011

(51) Int. Cl.
*A01H 5/00* (2006.01)

(52) U.S. Cl.
USPC ..... Plt./226

(58) Field of Classification Search ..... Plt./226
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Sambucus* named 'Eiffel 1' characterized by its upright, columnar plant habit, its dark purple foliage, its dark purple mature stems, its pink flowers and its large, dark black-purple berries.

2 Drawing Sheets

Genus/species: *Sambucus nigra.*
Varietal denomination: 'Eiffel 1'.

RELATED APPLICATIONS

This application is related to an application filed for a cultivar derived from the same parentage entitled *Sambucus* Plant Named 'Gerda' (U.S. Plant Pat. No. 12,305).

BACKGROUND OF THE INVENTION

The present invention relates to a new and distinct cultivar of *Sambucus nigra* and will be referred to hereafter by its cultivar name, 'Eiffel 1'. 'Eiffel 1' represents a new cultivar of Elderberry a deciduous shrub grown for landscape use.

The new *Sambucus* originated from a breeding program conducted by the Inventor in West Mailing, Kent, United Kingdom. An initial cross was made in 1990 between 'Pyramidalis' (not patented) and 'Guincho Purple' (not patented). 'Eiffel 1' arose from a cross made in June 1993 from two unnamed selected seedlings from the initial cross as the parent plants. 'Eiffel 1' was selected in 2000 as a single unique plant from amongst the 300 seedlings that has been planted out for evaluation in 1994 and propagated plants were grown in further trials through summer of 2010 to evaluate its mature stature and characteristics.

Asexual reproduction of the new cultivar was first accomplished by stem cuttings by the Inventor in East Mailing, Kent, United Kingdom in summer of 2000. The characteristics of this cultivar have been determined to be stable and are reproduced true to type in successive generations.

SUMMARY OF THE INVENTION

The following traits have been repeatedly observed and represent the characteristics of the new *Sambucus*. These attributes in combination distinguish 'Eiffel 1' as a distinct cultivar of *Sambucus.*

1. 'Eiffel 1' exhibits an upright, columnar plant habit.
2. 'Eiffel 1' exhibits foliage that is very dark purple in color.
3. 'Eiffel 1' exhibits stems that mature to a dark purple color.

4. 'Eiffel 1' exhibits pink flowers.
5. 'Eiffel 1' exhibits large berries that mature to a very dark black-purple color.

'Eiffel 1' can be readily distinguished from its parent plants. The male parent differs in having had foliage that is crinkled and unattractive, and having a less columnar plant habit. The female parent differs in having white flowers. 'Eiffel 1' can also be compared to the plants used in the first generation of the parents. 'Pyramidalis' is similar to 'Eiffel 1' in having an erect plant habit, however 'Pyramidalis' differs from 'Eiffel 1' in having green foliage and creamy white flowers. 'Guincho Purple' differs from 'Eiffel 1' in having a more spreading plant habit, having foliage that is lighter purple and more bronze in color and flowers that are creamy white in color with pink anthers. 'Eiffel 1' can be most closely compared to 'Gerda' that arose from the same parentage as 'Eiffel 1'. 'Gerda' is very similar in foliage and flower coloration, however the habit of 'Gerda' is spreading and not columnar. 'Eiffel 1' can also be compared to the cultivars 'Eva' (U.S. Plant Pat. No. 15,575) and 'Thundercloud' (not patented). 'Eva' is similar to 'Eiffel 1' in having dark purple foliage, however 'Eva' differs from 'Eiffel 1' in having laciniate leaves and in having a spreading plant habit. 'Thundercloud' differs from 'Eiffel 1' in having lighter purple foliage, a spreading and more open plant habit, smaller leaves and leaflets, and in being less robust.

BRIEF DESCRIPTION OF THE DRAWING

The accompanying photographs illustrate the characteristics of the new cultivar of *Sambucus.*

The photograph in FIG. 1 was taken of a 2 and one-half year-old plant as grown in a trial plot at a nursery in North Wales, United Kingdom and provides a side view of 'Eiffel 1' in bloom.

The photographs in FIG. 2 and FIG. 3 were taken of a two year-old plant as grown in a garden in Maldon, Essex, United Kingdom.

BOTANICAL DESCRIPTION OF THE PLANT

Figure 1:
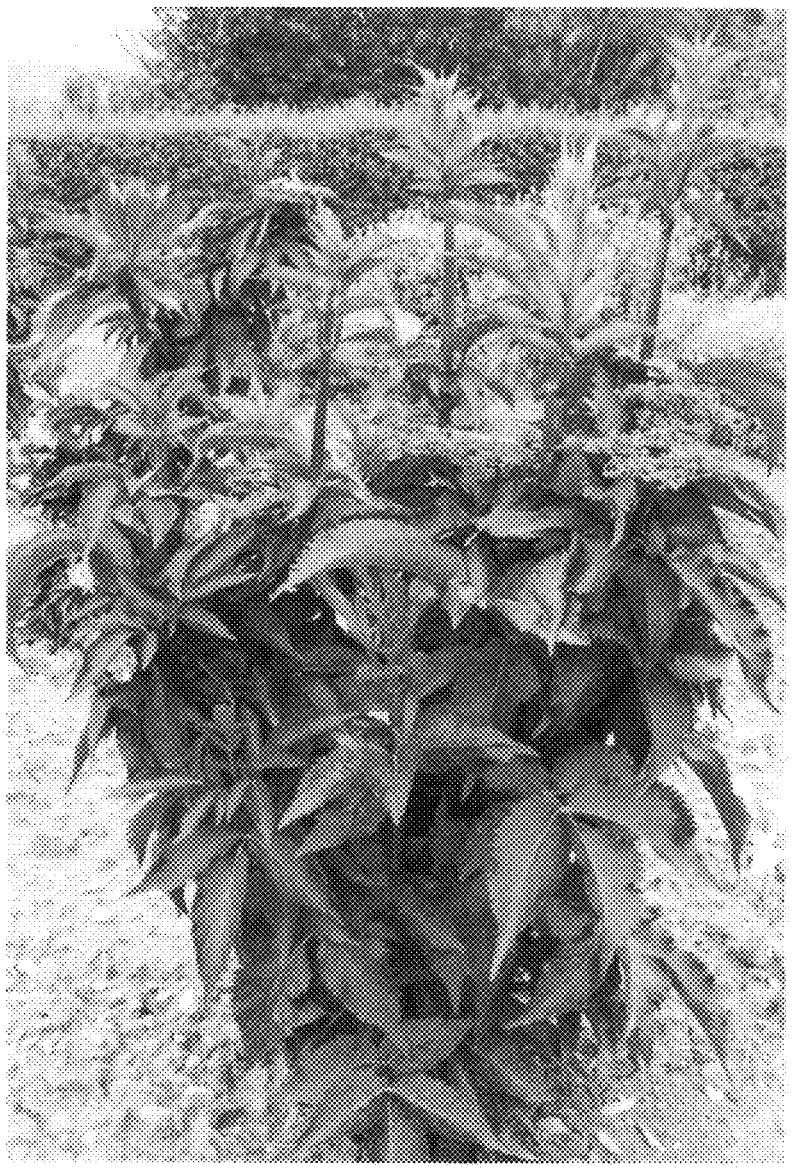
Figure 2:
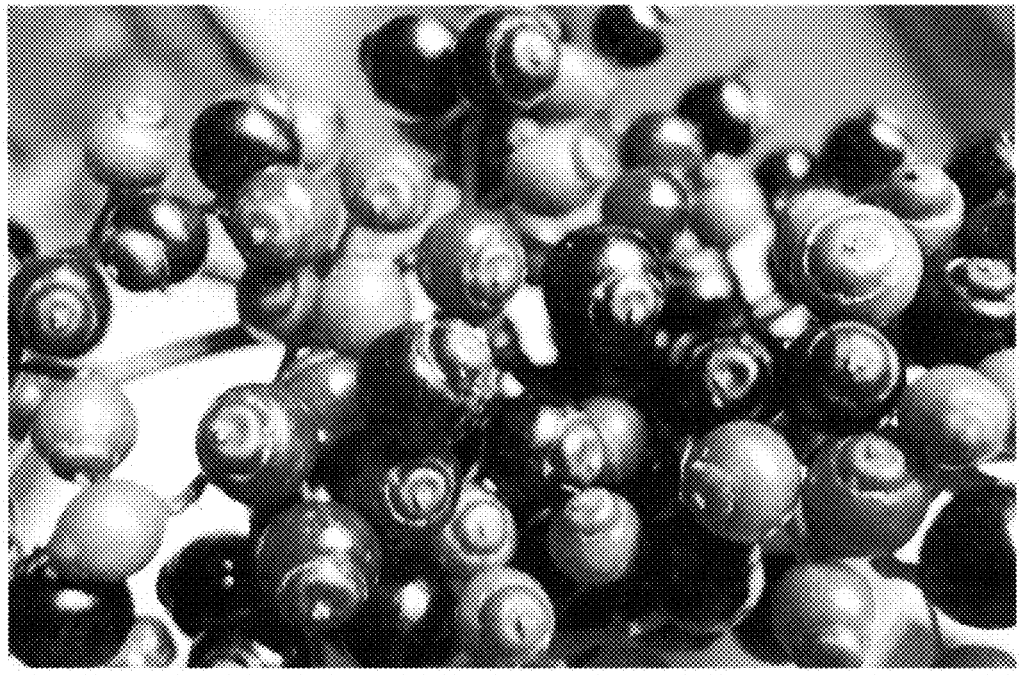
FIG. 2 provides a close-up view of the developing fruit and FIG. 3 provides a close-up view of a leave of 'Eiffel 1'. The colors in the photograph may differ slightly from the color values cited in the detailed botanical description, which accurately describe the colors of the new *Sambucus*.
Figure 3:
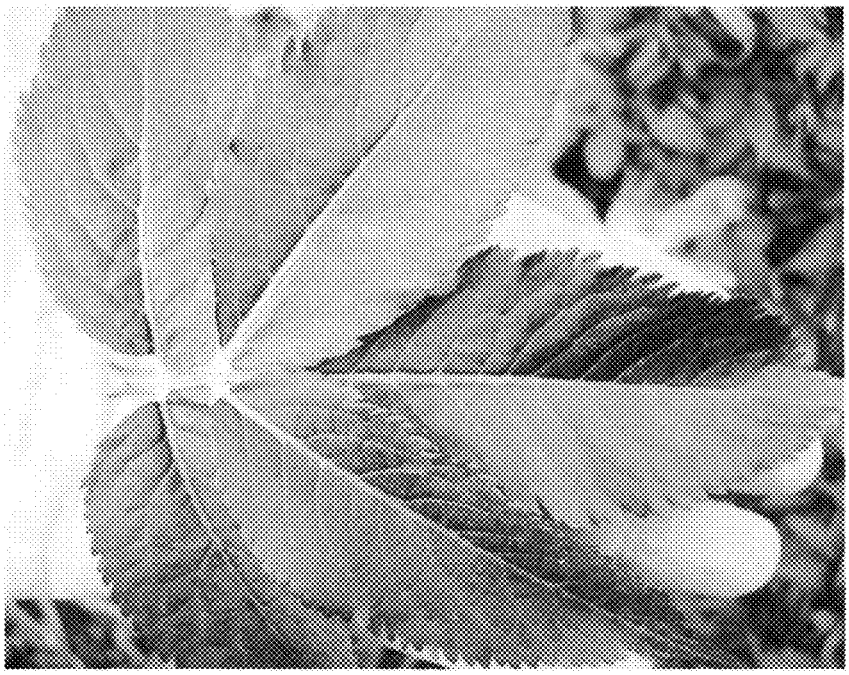

The following is a detailed description of two year-old plants of the new cultivar as grown outdoors in a trial plot in Liss, Hampshire, England. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant habit*.—Upright, columnar form.

*Blooming period*.—May to July in the United Kingdom.

*Height and spread*.—3 m in height and 2 m in spread.

*Plant type*.—Deciduous shrub.

*Cold hardiness*.—At least in U.S.D.A. Zone 5.

*Diseases and pest resistance*.—No susceptibility or resistance to diseases or pests has been observed.

*Root description*.—Fibrous.

*Growth rate*.—Moderately vigorous.

*Propagation*.—Nodal or internodal softwood stem cuttings.

Branch description:

*Branch color*.—Young stems; 197A and suffused with 79A, mature stem; 187A, 1 year-old shoots are 201A to 201C with lenticels; 0.5 mm in diameter and 1 mm in length, 197A in color, oval in shape and raised, bark on older stems; 199C.

*Branch size*.—Up to 3 m in length, up to 8 mm in diameter.

*Stem shape*.—Square.

*Branch surface*.—Glabrous, smooth, slight sheen when young, mature bark is furrowed.

*Branch habit*.—Primarily densely foliaged basal branches, branches held at a 45° angle at emergence and become upright, potential for lateral branches any node if pruned.

Foliage description:

*Leaf shape*.—Ovate to elliptic.

*Leaf division*.—Pinnate, typically with 5 leaflets.

*Leaf attachment*.—Petiolate.

*Leaf arrangement*.—Opposite/subopposite.

*Leaf fragrance*.—Foetid, typical of species.

*Internode length*.—Average of 45 cm.

*Leaf size*.—An average of 14 cm in length and 13 cm in width.

*Leaflet size*.—Up to 9.5 cm in length and 5 cm in width.

*Leaflet base*.—Rounded, unequal.

*Leaflet apex*.—Acuminate.

*Leaflet venation*.—Pinnate, color on upper surface 194A tinged with N186C, color on lower surface 195A tinged with N186C.

*Leaflet margin*.—Serrate.

*Leaflet surface*.—Glabrous, metallic look on upper and lower surface with short colorless hairs along veins.

*Leaflet color*.—Leaf buds; 187A, spring foliage upper surface; N186B to N186C, spring foliage lower surface; N138B flushed with 186D, summer and fall foliage upper surface; a color between N189A and 147A, summer and fall foliage lower surface; N138B flushed with 186D.

*Petioles*.—About 2 cm in length, about 2 mm in width, surface sparsely pubescent, N186C in color with channel on upper surface 191A, petiolules are similar in petiole characteristics but about 2 mm in length and width.

*Petiole shape*.—Flattened on upper surface and rounded on lower surface.

Flower description:

*Inflorescence type*.—Flat polychasium with umbel-like cyme, produced on at least 50% of overwintered stems.

*Inflorescence size*.—About 20 cm in diameter and 3 cm in depth.

*Flower fragrance*.—Musty muscatel.

*Flower lastingness*.—2 to 3 weeks.

*Flower bud description*.—Globose in shape, an average of 2 mm in diameter and height, 186C to 186B in color.

*Flower quantity*.—About 200 flowers per inflorescence.

*Flower size*.—About 6 to 7 mm in diameter and 0.3 mm in depth.

*Flower type*.—Rotate.

*Petal description*.—5, broadly ovate in shape, margin is entire, rounded apex, rounded base, upper and lower surface is glabrous.

*Petal size*.—About 2 mm in length and width.

*Petal color*.—Upper surface; 155D and tinged with 186D towards margins, fading to 155D with age, lower surface; 186B to 186C and fading to 155D near base.

*Sepal description*.—5, triangular in shape, entire margin, acute apex, rounded base, about 1 mm in length and 0.5 mm width, glabrous on upper and lower surface, color 177B.

*Peduncles*.—Rounded with flattened upper side in shape, about 4 cm in length and 3 mm in diameter, glabrous surface, 146C in color with sun exposed side overlaid with N186C.

*Pedicels*.—Rounded with flattened upper side in shape, about 4 mm in length and 0.5 mm in diameter, glabrous surface, 194D in color.

Reproductive organs:

*Gynoecium*.—1, style is distinguishable, stigma is <1 mm in diameter, flattened and sessile to ovary, and 155B in color and faintly tinged with 186D, ovary is ovoid in shape, superior, 1 mm in width and height, and 155B in color and faintly tinged with 186D.

*Androecium*.—5, anthers 1 mm in length and 185B in color, filaments 1.5 mm in length and 155B in color, pollen is abundant and 13D in color.

*Fruit and seed*.—Fruit; present in August to October in the United Kingdom, globose in shape in loose corymb, N187A in color and 186A when fully ripe, about 8 mm in diameter, flesh 145B in color, seed; approximately 3, 1 mm in diameter and 3 to 4 mm in length, 164A to 164C in color.

It is claimed:

1. A new and distinct cultivar of *Sambucus* plant named 'Eiffel 1' substantially as herein illustrated and described.

* * * * *